United States Patent [19]

Cherkofsky et al.

[11] 4,190,666

[45] Feb. 26, 1980

[54] ANTI-INFLAMMATORY 4,5-DIARLY-2-(SUBSTITUTED-THIO)IMIDAZOLES AND THEIR CORRESPONDING SULFOXIDES AND SULFONES

[75] Inventors: Saul C. Cherkofsky, Wilmington, Del.; Thomas R. Sharpe, Fort Salonga, N.Y.

[73] Assignee: E. I. Du Pont de Nemours and Company, Wilmington, Del.

[21] Appl. No.: 876,864

[22] Filed: Feb. 10, 1978

Related U.S. Application Data

[63] Continuation-in-part of Ser. No. 779,805, Mar. 18, 1977, abandoned, which is a continuation-in-part of Ser. No. 691,282, Jun. 9, 1976, abandoned, which is a continuation-in-part of Ser. No. 603,650, Aug. 11, 1975, abandoned.

[51] Int. Cl.$^2$ .............. A61K 31/415; C07D 233/84; C07D 233/86

[52] U.S. Cl. .................. 424/274; 548/336; 548/337

[58] Field of Search ............... 548/336, 337; 424/274

[56] References Cited

U.S. PATENT DOCUMENTS

| | | | |
|---|---|---|---|
| 3,505,350 | 4/1970 | Doebel et al. | 548/317 |
| 3,636,003 | 1/1972 | Doebel et al. | 548/337 |
| 3,651,080 | 3/1972 | Doebel et al. | 548/337 |
| 3,707,475 | 12/1972 | Lombardino | 548/342 |

FOREIGN PATENT DOCUMENTS 487073  8/1976  U.S.S.R. .................. 548/337

OTHER PUBLICATIONS

Zauer et al., Chem. Ber., vol. 106 (1973), pp. 1628–1636.
Bhatt et al., Current Science, vol. 17 (1948), pp. 184 and 185.
Fetter et al., Tetrahedron, vol. 27 (1971), pp. 5933–5941.

*Primary Examiner*—Richard Raymond

[57] ABSTRACT

Anti-inflammatory 4,5-diaryl-2-(substituted-thio)imidazols and their corresponding sulfoxides and sulfones useful for treating arthritis and related diseases.

82 Claims, No Drawings

ANTI-INFLAMMATORY 4,5-DIARLY-2-(SUBSTITUTED-THIO)IMIDAZOLES AND THEIR CORRESPONDING SULFOXIDES AND SULFONES

CROSS-REFERENCE TO RELATED APPLICATION

This application is a continuation-in-part of our co-pending application Ser. No. 779,805 filed Mar. 18, 1977, now abandoned, which is a continuation-in-part of Ser. No. 691,282 filed June 9, 1976 now abandoned which is a continuation-in-part of application Ser. No. 603,650, filed Aug. 11, 1975, now abandoned.

BACKGROUND

This invention relates to anti-inflammatory imidazoles.

Lombardino, in U.S. Pat. No. 3,707,475 discloses anti-inflammatory 4,5-diaryl-2-substituted imidazoles.

Doebel, in U.S. Pat. Nos. 3,505,350 and 3,651,080, respectively, discloses anti-inflammatory 4-alkyl-5-aryl-1-substituted-2-mercapto imidazoles and 4-alkyl-2-alkylthio-5-aryl-1-substituted imidazoles.

Zauer, K., et al., in Chem. Ber. 106, 1638 (1973), disclose 4,5-bis(4-methoxyphenyl)-2-methylthioimidazole and 4,5-bis(4-chlorophenyl)-2-methylthioimidazole but do not suggest any use.

A number of references, such as Current Sci. India 17, 184–85 (1948) and Acta. Chem. Acad. Sci. Hung. 79 (2) 197–212 (1973) disclose 2-(substituted-thio)-4,5-diphenyl imidazoles and 1-methyl-2-(substituted thio)-4,5-diphenyl imidazoles with substituents such as methyl, propyl, allyl, and acetonyl.

There is a continuing need for safe and effective anti-inflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and anti-inflammatory drugs are often used in their treatment. The usefulness of most commercial anti-inflammatories is limited because of toxicity and adverse side-effects. Many produce gastric irritation and other effects, such as changes in blood cells and central nervous system. Adreno-cortical steroids produce gastric irritation and suppression of normal adrenal function.

The Journal of the America Medical Association, Vol. 224, No. 5 (Supplement), 1973 "Primer on the Rheumatic Diseases" states that "Immunologic reactions appear to play a major role in the perpetuation of rheumatoid inflammation." Widely used non-steroidal anti-inflammatory drugs, such as aspirin, indomethacin, phenylbutazone and ibuprofen have no effect on these immunologic reactions, but merely relieve the symptoms of the inflammatory response; these drugs do not stop the progressive and ultimately destructive processes of rheumatoid arthritis. Immunosuppressive drugs, such as cyclophosphamide, are effective in the treatment of rheumatoid arthritis, but are too toxic for wide-spread use.

The present invention results from efforts to develop new anti-arthritic compounds with good anti-inflammatory and immunoregulatory activity and minimal side effects that could be more effective in treating arthritis than presently available drugs.

Compounds of this invention have demonstrated unique properties in several tests of anti-inflammatory and immunoregulatory activity. The biological profiles of these compounds are different from non-steroidal anti-inflammatory drugs and immunosuppressive drugs. These unique properties provide for a novel approach to the treatment of rheumatoid arthritis, and may also be useful in the treatment of other diseases involving altered immune states.

In addition to anti-inflammatory and immunoregulating properties, compounds of this invention have demonstrated analgesic activity in a test procedure. This additional property is desirable in treatment of arthritis or related diseases; however, such compounds can be employed solely to alleviate pain.

SUMMARY

According to this invention there is provided compounds of formula I and pharmaceutically suitable salts, processes for their manufacture, pharmaceutical compositions containing them, and methods of using them to treat arthritis or alleviate pain in mammals.

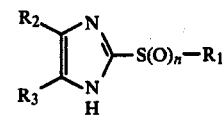

where
n=0, 1, or 2;
$R_1 = C_1$–$C_8$ alkyl; allyl; vinyl; —$CH_2COCH_3$; —$CH_2$-$S(O)_mCH_3$, where m=0, 1, or 2; mono— or polyhalo—$C_1$–$C_8$ alkyl;
$R_2$ and $R_3$, the same or different =

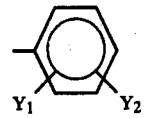

$Y_1$ or $Y_2$, the same or different = hydrogen, $C_1$–$C_4$ alkoxy, acetoxy, $C_1$–$C_4$ alkyl, Cl, F, $CF_3$, —$N(CH_3)_2$, $NO_2$, $CH_3S$—, $CH_3SO_2$, or $Y_1$ and $Y_2$ taken together forming a dioxymethylene bridge;
provided, when $R_1 = C_1$–$C_8$ alkyl, $C_3$–$C_8$ haloalkyl with halogen substituted at the 3 through 8 position, allyl, or acetonyl, both $Y_1$ and $Y_2$ cannot be H.

Several compounds of formula I are not novel; those where n=0, $R_1 = CH_3$, and both $Y_1$ and $Y_2$ are either p-Cl, or p-OCH$_3$. Also since parent application Ser. No. 603,650 was filed there has been disclosed a compound where n=0, $Y_1$ and $Y_2$ both = hydrogen and $R_1$ = vinyl.

The proviso in formula I is necessary to exclude compounds that are not sufficiently active to have practical utility.

DETAILED DESCRIPTION

Preferred Compounds

Compounds preferred for their antiarthritic activity are those where $R_1 = $—$CF_2CF_2H$.

Also preferred are those compounds where $R_1 = CF_3$.

Also preferred are those compounds where
$R_2$ and $R_3$, independently, =

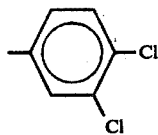

or

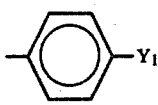

where
$Y_1$ = H, Cl, or F;
More preferred are those compounds where:
$R_1$ = —$CF_2CF_2H$;
$R_2$ and $R_3$, independently, =

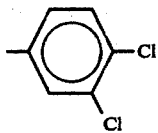

or

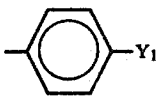

where
$Y_1$ = H, Cl, or F; and
n = 0, 1, or 2.
Also more preferred are those compounds where
$R_1$ = $CF_3$;
$R_2$ and $R_3$, independently, =

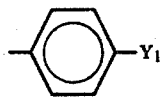

where
$Y_1$ = H, Cl, or F; and
n = 0, 1, or 2.
Specifically preferred are the following compounds:
4,5-bis(4-fluorophenyl)-2-(1,1,2,2-tetrafluoroethylsulfonyl)imidazole;
4(or 5)-(4-fluorophenyl)-5(or 4)-phenyl-2-(1,1,2,2-tetrafluoroethylsulfonyl)imidazole;
4,5-bis(4-chlorophenyl)-2-(1,1,2,2-tetrafluoroethylsulfonyl)imidazole;
4(or 5)-(4-chlorophenyl)-5(or 4)-phenyl-2-(1,1,2,2-tetrafluoroethylsulfonyl)imidazole;
4,5-diphenyl-2-(1,1,2,2-tetrafluoroethylsulfonyl)imidazole;
4,5-diphenyl-2-(1,1,2,2-tetrafluoroethylthio)imidazole.
4,5-diphenyl-2-trifluoromethylsulfonylimidazole;
4,5-bis(p-fluorophenyl)-2-trifluoromethylthioimidazole;
4,5-bis(p-fluorophenyl)-2-trifluoromethylsulfonylimidazole.
4(or 5)-(3,4-dichlorophenyl)-5(or 4)-phenyl-2-(1,1,2,2-tetrafluoroethylsulfonyl)imidazole.

The following compounds are preferred because of their analgesic activity:

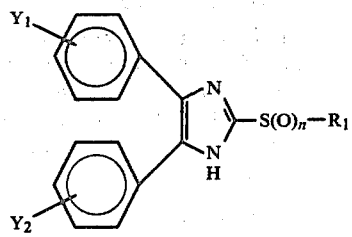

where
$R_1$ = $C_1$–$C_4$ alkyl, monohalo- and polyhalo-$C_1$–$C_4$ alkyl;
$Y_1$ and $Y_2$, the same or different, = H, 2-methoxy, 4-methoxy, 2-ethoxy, 4-ethoxy, 2-chloro, or 4-chloro;
n = 0, 1, or 2.
More preferred are those compounds where
$R_1$ = polyhalo-$C_1$–$C_2$ alkyl;
$Y_1$ and $Y_2$, the same or different, = H, 2-methoxy, 4-methoxy, 2-ethoxy, 4-ethoxy, 2-chloro, or 4-chloro; provided that, at least one of $Y_1$ and $Y_2$ = 4-methoxy or 4-ethoxy;
n = 0, 1, or 2.
Specifically preferred for analgesic activity are these compounds:
4,5-bis(4-methoxyphenyl)-2-(1,1,2-trifluoroethylsulfonyl)imidazole;
4,5-bis(4-methoxyphenyl)-2-(1,1,2,2-tetrafluoroethylsulfonyl)imidazole;
4,5-bis(4-methoxyphenyl)-2-(2,2,2-trifluoroethylthio)imidazole;
4,5-bis(4-methoxyphenyl)-2-(2,2,2-trifluoroethylsulfinyl)imidazole;
4,5-bis(4-methoxyphenyl)-2-(2,2,2-trifluoroethylsulfonyl)imidazole;
4,5-bis(4-methoxyphenyl)-2-(trifluoromethylsulfonyl)imidazole.

Tautomers

When $R_2$ and $R_3$ are different, the following two structures are tautomers:

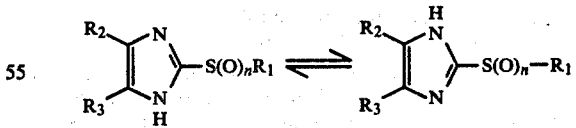

Pharmaceutical Salts

Pharmaceutically suitable salts of compounds where n = 0 include pharmaceutically suitable acid addition salts, preferably formed from mineral acids, and include hydrochloride, nitrate and sulfate. The acid preferably has a $pK_a$ value not greater than 2.5.

Pharmaceutically suitable salts of compounds where n = 1 or 2 include those of certain metals, such as sodium, potassium, and calcium.

The salts can be prepared by well known methods in the prior art of preparing salts.

Synthesis

The compounds of Example I can be prepared as follows: benzoin or an appropriately substituted benzoin prepared as described in Ide, W. S. and Buck, J. S., *Organic Reactions*, Vol. IV, P. 629, is condensed with thiourea in refluxing dimethylformamide or other high boiling, polar solvents to give a 4,5-diaryl-2-mercaptoimidazole. A similar condensation procedure is described in Kochergin, P. M., *Zhur. Obshchei Khim.*, 31, 1093 (1961); *Chem. Abstr.* 55, 23503f.

4,5-Diaryl-2-mercaptoimidazoles can also be prepared by heating 4,5-diarylimidazoles with sulfur at temperatures in the range of 150°–300° either with or without solvent. One suitable solvent for this reaction is tetramethylene sulfone. This procedure is analogous to the conversion of 1-methylbenzimidazole to 2-mercapto-1-methylbenzimidazole as described in A. V. El'tsov and K. M. Krivozheiko, ZhOrKh, 2, 189 (1966).

Preferably, reaction of the acyloins above with ammonium thiocyanate at lower temperatures in polar solvents such as ethanol or 1-propanol can be used to prepare 4,5-disubstituted-2-mercaptoimidazoles.

The appropriate $R_1$ group can be introduced by alkylating the 4,5-diaryl-2-mercaptoimidazole with a suitable alkylating agent such as ethyl iodide or 2,2,2-trifluoroethyl trichloromethanesulfonate. These procedures and the use of other alkylating agents can be found in the Examples.

Also, the 4,5-diaryl-2-mercaptoimidazole can be reacted with tetrafluoroethylene to provide 4,5-diaryl-2-(1,1,2,2-tetrafluoroethylthio)imidazole derivatives. Similar addition reactions of tetrafluoroethylene and other fluorinated olefins are described in England, D. C., et al., *J. Am. Chem. Soc.*, 82, 5116 (1960) and Rapp, K. E., et al., *J. Am. Chem. Soc.*, 72, 3642 (1950). For the purpose of this disclosure tetrafluoroethylene and other fluorinated olefins used are considered alkylating agents.

The 4,5-diaryl-2-(substituted-thio) imidazole can then be oxidized to the corresponding sulfoxide or sulfone by using oxidizing agents such as m-chloro-perbenzoic acid, Tweit, R. C., et al., *J. Med. Chem.*, 16, 1161 (1973), sodium metaperiodate, Leonard, N. J. and Johnson, C. R., *J. Org. Chem.* 27, 282 (1962), hydrogen peroxide, Kochergin, P.M. and Shchukina, M. N., *J. Gen. Chem. U.S.S.R.*, 25, 2289 (1955), or potassium permanganate, Rapp, K. E. et al., loc. cit.

Compounds of formula I can also be made by contacting an N-protected diarylimidazole (such as 4,5-diphenyl-1-(2-tetrahydropyranyl)imidazole, 1-benzyloxymethyl-4,5-diphenylimidazole or 1-benzenesulfonyl-4,5-diphenylimidazole, for example) with a strong base, such as n-butyllithium and the like, then with a fluorinated alkylsulfenyl halide, disulfide, or sulfonic anhydride. Proper choice of the protecting group and the workup conditions allows isolation of the desired 4,5-diaryl-2-(substituted thio or sulfonyl) imidazole directly. Compounds where $R_1=CF_3$ can be conveniently prepared by this method.

The preparation of these compounds is further illustrated by the following Examples. Parts are by weight and temperatures are in degrees centigrade unless otherwise stated.

EXAMPLE 1

4,5-Diphenyl-2-(2,2,2-trifluoroethylthio)imidazole

A mixture of 4,5-diphenyl-2-mercaptoimidazole (71.9 g., 0.285 mole), 2,2,2-trifluoroethyl trichloromethanesulfonate (80.3 g., 0.285 mole), triethylamine (28.8 g., 0.285 mole), and toluene (700 ml.) is refluxed under nitrogen for four hours. After cooling to room temperature there is recovered (by filtration) 13.4 g. of 4,5-diphenyl-2-mercaptoimidazole. The filtrate is washed twice with water, and upon cooling the organic phase the product crystallizes. There is obtained 46.2 g. (49%) of 4,5-diphenyl-2-(2,2,2-trifluoro-ethylthio) imidazole as nearly colorless crystals, m.p. 185.5–187°.

Anal. Calc'd. for $C_{17}H_{13}F_3N_2S$: C, 61.06; H, 3.92 N, 8.38. Found: C, 61.28; H, 3.97; N, 8.49.

EXAMPLE 2

4,5-Diphenyl-2-(2,2,2-trifluoroethylsulfinyl)imidazole

To a mixture of 4,5-diphenyl-2-(2,2,2-trifluoro-ethylthio)imidazole (13.9 g., 0.0416 mole) and chloroform (75 ml.) cooled in an ice bath is added dropwise 86.4% m-chloroperbenzoic acid (8.4 g., 0.042 mole) in chloroform (85 ml.). After stirring overnight the mixtures is washed with saturated sodium bicarbonate, dried with magnesium sulfate and stripped of solvent to afford 12.3 g. of crude product. Recrystallization from toluene gives 10.1 g. (69%) of 4,5-diphenyl-2-(2,2,2-trifluoroethylsulfinyl)imidazole as colorless prisms, m.p. 198° (dec.).

Anal. Calc'd. for $C_{17}H_{13}F_3N_2OS$: C, 58.28; H, 3.74; N, 8.00. Found: C, 58.27; H, 3.76; N, 8.10.

EXAMPLE 3

4,5-Diphenyl-2-(2,2,2-trifluoroethylsulfonyl)imidazole

To a mixture of 4,5-diphenyl-2-(2,2,2-trifluoro-ethylthio)imidazole (15.7 g., 0.0470 mole) and chloroform (100 ml.) cooled in an ice bath is added dropwise 86.4% m-chloroperbenzoic acid (19.0 g., 0.0952 mole) in chloroform (200 ml.). After stirring for four days at room temperature, tetrahydrofuran is added, and the mixture is washed with saturated sodium bicarbonate, dried with magnesium sulfate, and stripped of solvent to give 16.9 g. of crude product. After two recrystallizations from acetonitrile there is obtained 8.8 g. (51%) of 4,5-diphenyl-2-(2,2,2-trifluoroethyl-sulfonyl)imidazole as colorless needles, m.p. 228° (dec.).

Anal. Calc'd. for $C_{17}H_{13}F_3N_2O_2S$: C, 55.73; H, 3.58; N, 7.65; F, 15.56. Found: C, 56.18, 56.06; H, 3.94, 3.95; N, 7.45, 7.52; F, 15.44.

EXAMPLE 4

4,5-bis-(4-Methoxyphenyl)-2-(2,2,2-trifluoroethylthio)imidazole

A mixture of 2-mercapto-4,5-bis(4-methoxyphenyl)-imidazole (31.2 g., 0.100 mole), 2,2,2-trifluorethyl trichloromethanesulfonate (31.0 g., 0.110 mole), triethylamine (11.1 g., 0.110 mole), and toluene (300 ml.) is refluxed for six hours under nitrogen. The mixture is cooled, washed three times with water, dried with magnesium sulfate, and concentrated to give 43.4 g. of crude product which is chromatographed on a column containing one pound of silica gel eluting with chloroform. The residue from the major fraction is recrystallized from methylcyclohexane to give 21.5 g. (55%) of 4,5-bis(4-methoxyphenyl)-2-(2,2,2-trifluoroethylthio)- imidazole as nearly colorless crystals, m.p. 119°–120°. A polymorphic form has m.p. 150°–151°.

Anal. Calc'd. for $C_{19}H_{17}F_3N_2O_2S$: C, 57.86; H, 4.34; N, 7.10. Found: C, 57.96; H, 4.01; N, 7.09.

EXAMPLE 5

4,5-bis(4-Methoxyphenyl)-2-(2,2,2-trifluoroethylsulfinyl)-imidazole

By using 4,5-bis(4-methoxyphenyl)-2-(2,2,2-trifluoroethylthio)imidazole in place of the 4,5-diphenyl-2-(2,2,2-trifluoroethylthio)imidazole of Example 2 one obtains as product 4,5-bis(4-methoxyphenyl)-2-(2,2,2-trifluoroethyl-sulfinyl)imidazole. Recrystallization of the crude product from aqueous ethanol gives an 83% yield of pure product, m.p. 19.5° (dec.).

Anal. Calc'd. for $C_{19}H_{17}F_3N_2O_3S$: C, 55.60; H, 4.18; N, 6.83. Found: C, 55.52; H, 3.80; N, 6.77.

EXAMPLE 6

4,5-bis(4-Methoxyphenyl)-2-(2,2,2-trifluoroethylsulfonyl)-imidazole

To a mixture of 4,5bis(4-methoxyphenyl)-2-(2,2,2-trifluoroethylthio)imidazole (6.0 g., 0.015 mole) and chloroform (75ml.) cooled in an ice bath is added dropwise 86.4% m-chloroperbenzoic acid (6.1 g., 0.031 mole) in chloroform (75 ml.). After stirring overnight at room temperature the mixture is washed with saturated sodium bicarbonate, dried with magnesium sulfate, and concentrated to give 7.1 g. of crude product. Recrystallization from 1-chlorobutane gives pure 4,5-bis(4-methoxyphenyl)-2-(2,2,2-trifluoroethylsulfonyl)-imidazole as colorless needles, m.p. 173°–174°.

Anal. Calc'd. for $C_{19}H_{17}F_3N_2O_4S$: C, 53.51; H, 4.02; N, 6.57. Found: C, 53.47, 53.81; H, 4.06, 3.69; N, 6.55, 6.59.

EXAMPLE 7

4,5-bis(4-Chlorophenyl)-2-(2,2,2-trifluoroethylthio)imidazole

A mixture of 4,5-bis(4-chlorophenyl)-2-mercaptoimidazole (32.1 g., 0.100 mole), 2,2,2-trifluoroethyl trichloromethanesulfonate (28.1 g., 0.100 mole), sodium methoxide (5.9 g., 0.109 mole), and ethanol (300 ml.) is refluxed for three hours. The reaction mixture is poured into water, and the solid is collected by filtration, washed with water, and dried. This solid (43.9 g.) is then stirred overnight in ethyl acetate (400 ml.). The mixture is filtered, and the filtrate is stripped of solvent to give 21.7 g. of a residue. This residue is recrystallized from toluene to give 15.1 g. (37%) of pure 4,5-bis(4-chlorophenyl)-2-(2,2,2-trifluoroethylthio)imidazole as colorless crystals, m.p. 212°–213°.

Anal. Calc'd for $C_{17}H_{11}Cl_2F_3N_2S$: C, 50.63; H, 2.75; N, 6.95. Found: C, 50.87; H, 3.05; N, 6.69.

EXAMPLE 8

4,5-bis(4-Chlrophenyl)-2-(2,2,2-trifluoroethylsulfinyl)-imidazole

By using 4,5-bis(4-chlorophenyl)-2,2,2-trifluoroethylthio)imidazole in place of the 4,5-diphenyl-2-(2,2,2-trifluoroethylthio)imidazole of Example 2 one obtains as product 4,5-bis(4-chlorophenyl)-2-(2,2,2-trifluoroethyl-sulfinyl)imidazole. Recrystallization of the crude product from acetonitrile gives a 77% yield of pure product, m.p. 214° (dec.).

Anal. Calc'd. for $C_{17}H_{11}Cl_2F_3N_2OS$: C, 48.70; H, 2,64; N, 6.68. Found: C, 48.97; H, 2.89; N, 6.47.

EXAMPLE 9

4,5-bis(4-Chlorophenyl)-2-(2,2,2-trifluoroethylsulfonyl)imidazole

To a mixture of 4,5-bis(4-chlorophenyl)-2-(2,2,2-trifluoroethylthio)imidazole (5.3 g., 0.013 mole) and chloroform (50 ml.) cooled in an ice bath is added dropwise 86.4% m-chloroperbenzoic acid (5.3 g., 0.027 mole) in chloroform (60 ml.). After stirring overnight at room temperature, the mixture is refluxed for fifteen minutes, cooled, and the solid is collected and washed with cold chloroform. The solid is then dissolved in a mixture of ether and tetrahydrofuran, and the resulting solution is washed with saturated sodium bicarbonate. The organic phase is dried with magnesium sulfate and stripped of solvent to give 5.8 g. of a colorless, solid residue which is recrystallized from nitro-methane (125 ml.). There is obtained 4.1 g. (72%) of pure 4,5-bis(4-chlorophenyl)-2-(2,2,2-trifluoroethylsulfonyl)imidazole as colorless needles, m.p. 241° (dec.).

Anal. Calc'd for $C_{17}H_{11}Cl_2F_3N_2O_2S$: C, 46.91; H, 2.55; N, 6.44. Found: C, 47.13, 47.29; H, 2.67, 2.58; N, 6.56, 6.58.

EXAMPLE 10

2-Ethylthio-4,5-bis(4-methoxyphenyl)imidazole

To a suspension of 2-mercapto-4,5-bis(4-methoxyphenyl)imidazole (31,2 g., 0.100 mole) in methanol (200 ml.) is added in one portion sodium methoxide (6.5 g., 0.12 mole), and the mixture is stirred for 15 min. A solution of iodoethane (17.1 g., 0.11 mole) in methanol (50 ml.) is added dropwise, and the mixture is heated at reflux for 4.5 hours. After stirring overnight at room temperature, the mixture is poured into water, and the solid which precipitates is collected, washed with water, and dried to give 33.0 g. of crude product. Recrystallization from aqueous ethanol gives 28.8 g. (85%) of pure 2-ethylthio-4,5-bis(4-methoxyphenyl)imidazole, m.p. 108°–109°.

Anal. Calc'd. for $C_{19}H_{20}N_2O_2S$: C, 67.03; H, 5.92; N, 8.23. Found: C, 66.96; H, 6.10; N, 7.85.

EXAMPLE 11

2-Allylthio-4,5-bis(4-methoxyphenyl)imidazole

A mixture of 2-mercapto-4,5-bis(4-methoxyphenyl) imidazole (31.2 g., 0.100 mole), allyl bromide (13.1 g., 0.108 mole), triethylamine (20.2 g., 0.200 mole), and chloroform (500 ml.) is heated overnight at reflux. Allyl bromide (4.8 g., 0.040 mole) is then added and reflux continued for two hours. Two additional portions (4.8 g.) of allyl bromide are added followed in each instance by a two-hour relux period. The clear solution is cooled, washed three times with water, dried with magnesium sulfate, and concentrated. The residue is triturated with ether, and the solid is collected to give 31.5 g. of crude product. Recrystallization from aqueous ethanol gives 26.7 g. (76%) of pure 2-allylthio-4,5-bis(4-methoxyphenyl)imidazole, m.p. 167°–167.5°.

Anal. Calc'd for $C_{20}H_{20}N_2O_2S$: C, 68.16; H, 5,72; N, 7.95. Found: C, 67.22; H, 5.87; N, 7.81.

EXAMPLE 12

4,5-bis(4-Methoxyphenyl)-2-(methylthiomethylthio)imidazole

By substituting chloromethyl methyl sulfide for the allyl bromide of Example 11 one obtains as product 4,5-bis-(4-methoxyphenyl)-2-(methylthiomethylthio)imidazole, m.p. 171°–172°.

Anal. Calc'd. for $C_{19}H_{20}N_2O_2S_2$: C, 61.26; H, 5.41; N, 7.52. Found: C, 61.32; H, 5.57; N, 7.32.

EXAMPLE 13

2-Ethylsulfinyl-4,5-bis(4-methoxyphenyl)imidazole

To a solution of 2-ethylthio-4,5-bis(4-methoxyphenyl imidazole (10.2 g., 0.0300 mole) in dichloromethane (200 ml.) cooled in an ice bath is added dropwise a solution of 86.4% m-chloroperbenzoic acid (6.0 g., 0.030 mole) in dichloromethane (100 ml.). After stirring overnight at room temperature, the reaction mixture is washed with three portions (75 ml.) of saturated sodium bicarbonate. The organic phase is dried with magnesium sulfate and the solvent removed on a rotary evaporator. The residual oil is triturated with ether, and the resulting solid is collected and recrystallized from 1-chlorobutane (500 ml.) to give 7.5 g. (70%) of pure 2-ethylsulfinyl-4,5-bis(4-methoxyphenyl)imidazole, m.p. 161°–162°.

Anal. Calc'd. for $C_{19}H_{20}N_2O_3S$: C, 64.02; H, 5.66; N, 7.86. Found: C, 63.98; H, 5.59; N, 7.97.

EXAMPLE 14

2-Ethylsulfonyl-4,5-bis(4-methoxyphenyl)imidazole

By substituting 12.0 g. (0.060 mole) of 86.4% m-chloroperbenzoic acid in place of the 6.0 g. of 86.4% m-chloroperbenzoic acid of Example 13, one obtains after recrystallization from 1-chlorobutane (125 ml.) 6.0 g. (54%) of 2-ethylsulfonyl-4,5-bis(4-methoxyphenyl imidazole, m.p. 136°–137°.

Anal. Calc'd. for $C_{19}H_{20}N_2O_4S$: C, 61.27; H, 5.41; N, 7.52. Found: C, 61.47; H, 5.47; N, 7.35.

EXAMPLE 15

4,5-bis(4-Methoxyphenyl)-2-methylthioimidazole

By substituting iodomethane for the iodoethane of Example 10, one obtains as product 4,5-bis(4-methoxyphenyl)-2-methylthioimidazole, m.p. 157°–158.5°.

Anal. Calc'd. for $C_{18}H_{18}N_2O_2S$: C, 66.23; H, 5.56; N, 8.58. Found: C, 65.84; H, 5.53; SN, 8.46.

EXAMPLE 16

2-Acetonylthio-4,5-bis(4-methoxyphenyl)imidazole

To a stirred mixture of 2-mercapto-4,5-bis(4-methoxyphenyl)imidazole (31.2 g., 0.100 mole), triethylamine (11.0 g., 0.11 mole), and chloroform (500 ml.) is added chloroacetone (10.2 g., 0.11 mole) dropwise in chloroform (50 ml.). After stirring overnight at reflux, the reaction mixture is washed three times with water, dried with magnesium sulfate, and concentrated to give 32.0 g. of crude product. Chromatography (silica gel, chloroform) affords 27.0 g. (73%) of pure 2-acetonylthio-4,5-bis(4-methoxyphenyl)imidazole, m.p. 115°–117.5°.

Anal. Calc'd for $C_{20}H_{20}N_2O_3S$: C, 65.20; H, 5.47; N, 7.60. Found: C, 65.14; H, 5.42; N, 7.36.

EXAMPLE 17

4,5-bis(4-Methoxyphenyl)-2-(methylthiomethylsulfinyl)imidazole and
4,5-bis(4-methoxyphenyl)-2-(methylsulfinylmethylthio)imidazole To a solution of 4,5-bis(4-methoxyphenyl)-2-(methylthiomethylthio)imidazole (7.4 g., 0.020 mole) in dichloromethane (100 ml.) cooled in an ice bath is added a solution of 86.4% m-chloroperbenzoic acid (4.0 g., 0.020 mole) in dichloromethane (100 ml.). After stirring overnight at room temperature, the reaction mixture is washed three times with saturated sodium bicarbonate solution, dried with magnesium sulfate, and concentrated. The residue (7.5 g.) is then chromatographed on a column of silica gel which is eluted with a mixture of toluene and ethyl acetate.

The first pure compound to elute from the column is 4,5-bis(4-methoxyphenyl)-2-(methylthiomethylsulfinyl) imidazole, m.p. 142.5°–143.5°.

Anal. Calc'd. for $C_{19}H_{20}N_2O_3S_2$: C, 58.74; H, 5.19; N, 7.21. Found: C, 59.00; H, 5.13; N, 6.93.

Further elution of the column provides pure 4,5-bis(4-methoxyphenyl)-2-(methylsulfinylmethylthio)imidazole, m.p. 84.5°–86.5°.

Anal. Calc'd. for $C_{19}H_{20}N_2O_3S_2$: C, 58.74; H, 5.19; N, 7.21. Found: C, 58.85; H, 5.36; N, 6.94.

EXAMPLE 18

4,5-Diphenyl-2-(1,1,2,2-tetrafluoroethylthio)imidazole

To a stainless steel tube is added 4,5-diphenyl-2-mercaptoimidzaole (5.0 g., 0.020 mole) and dimethylformamide (50 ml.) which contains 0.5 ml. of a 40% methanol solution of benzyl trimethylammonium hydroxide. Subsequent to purging the tube several times with dry nitrogen, tetrafluoroethylene (2.2 g., 0.022 mole) is introduced. The tube is agitated for seven hours. The reaction mixture is poured into water, and the solid is collected and washed with water affording 5.7 g. of crude product. Column chromatography (silica gel, chloroform) provides 3.5 g. of pure 4,5-diphenyl-2-(1,1,2,2-tetrafluoroethylthio)imidazole, m.p. 212°–213°.

Anal. Calc'd. for $C_{17}H_{12}F_4N_2S$: C, 57.95; H, 3.43; N, 7.95. Found: C, 57.71; H, 3.70; N, 7.89.

EXAMPLE 19

4,5-bis(4-Methoxyphenyl)-2-vinylthioimidazole

To a stainless steel tube is added 4,5-bis(4-methoxyphenyl)-2-mercaptoimidazole (15.0 g., 0.05 mole), cuprous chloride (0.75 g.), and 100 ml. of dimethylformamide. The tube is cooled, evacuated, and then pressured with 1.3 g. of acetylene. The tube is heated at 150° with shaking for eight hours, cooled, and vented. The contents are diluted with 500 ml. of water, and 25 ml. of concentrated ammonium hydroxide is added. The aqueous mixture is extracted with ether (4×300 ml.). The combined ether extracts are backwashed with water (3×300 ml.) and then dried and concentrated on a rotary evaporator. The residue is chromatographed on a column containing 600 g. of silica gel (SilicAR® CC-7). The product is eluted with chloroform (cut 6–8, one liter each) to give after concentration 2.9 g. of crystals. A recrystallization from 1-chlorobutane/hexane gives 2.8 g. of pure product, m.p. 114°–115°.

Anal. Calc'd. for $C_{19}H_{18}N_2O_2S$: C, 67.43; H, 5.36; N, 8.28. Found: C, 67.17; H, 5.40; N, 8.42.

EXAMPLE 20

4,5-bis(4-Methoxyphenyl)-2-(1,1,2-trifluoroethylthio)imidazole

To a solution of 2-(2-bromo-1,1,2-trifluoroethylthio)-4,5-bis(4-methoxyphenyl)imidazole (14.2 g., 0.03 mole) in 150 ml. toluene is added tri-n-butyltin hydride (9.0 g., 0.03 mole). The mixture is refluxed for four hours. Another 9.0 g. (0.03 mole) of tri-n-butyltin hydride is added and the mixture is refluxed overnight. The mixture is then added directly to a column of 2 lb. of silica gel (SilicAR ® CC-7). Elution with toluene followed by toluene/ethyl acetate (95/5) gives 6.5 g. of crystalline product. A recrystallization from methylcyclohexane gives 5.6 g. of pure product, m.p. 143.5°-145°.

Anal. Calc'd. for $C_{19}H_{17}F_3N_2O_2S$: C, 57.86; H, 4.34; N, 7.10. Found: C, 57.95; H, 4.71; N, 7.04.

EXAMPLE 21

4,5-Diphenyl-2-(1,1,2-trifluoroethylthio)imidazole

By substituting 2-(2-bromo-1,1,2-trifluoroethylthio)-4,5-diphenylimidazole for the 2-(2-bromo-1,1,2-trifluoroethylthio)-4,5-bis(4-methoxyphenyl)imidazole of Example 20, one obtains as product 4,5-diphenyl-2-(1,1,2-trifluoroethylthio)imidazole, m.p. 225°-226.5°.

EXAMPLE 22

4,5-bis(4-Fluorophenyl)-2-(1,1,2,2-tetrafluoroethylsulfonyl)imidazole Sodium Salt A mixture of 4,51-bis(4-fluorophenyl)-2-(1,1,2,2-tetrafluoroethylsulfonyl)imidazole (5.0 g., 0.0119 mole), sodium methoxide (0.6 g., 0.0111 mole) and ether (300 ml.) is stirred overnight at room temperature. The solid is collected and washed with ether to give 2.1 g. of the sodium salt of 4,5-bis(4-fluorophenyl)-2-(1,1,2,2-tetrafluoroethylsulfonyl)imidazole, m.p. 290°-292°.

Anal. Calc'd. for $C_{17}H_9F_6N_2O_2SNa$: C, 46.16; H, 2.05; N, 6.33. Found: C, 45.98; H, 2.19; N, 6.07.

EXAMPLE 23

4,5-Diphenyl-2-(1,1,2,2-tetrafluoroethylsulfonl)imidazole Sodium Salt

By utilizing the procedure described in Example 22 and employing as starting material 4,5-diphenyl-2-(1,1,2,2-tetrafluoroethylsulfonyl)imidazole, one obtains as product, 4,5-diphenyl-2-(1,1,2,2-tetrafluoroethylsulfonyl)imidazole sodium salt, m.p. 296°-302° (dec.).

EXAMPLE 24

4,5-bis(4-Hydroxyphenyl)-2-(1,1,2,2-tetrafluoroethylsulfonyl)imidazole

A mixture of 4,5-bis(4-t-butoxyphenyl)-2-(1,1,2,2-tetrafluoroethylsulfonyl)imidazole and trifluoroacetic acid is stirred overnight at room temperature. The reaction mixture is poured into water, and work-up affords as product 4,5-bis(4-hydroxyphenyl)-2-(1,1,2,2-tetrafluoroethylsulfonyl)imidazole.

EXAMPLE 25

4,5-bis(4-Acetoxyphenyl)-2-(1,1,2,2-tetrafluoroethylsulfonyl)imidazole

A mixture of 4,5-bis(4-hydroxyphenyl)-2-(1,1,2,2-tetrafluoroethylsulfonyl)imidazole (0.1 mole), acetic anhydride (0.2 mole), and pyridine (500 ml.) is heated for two hrs. on the steam bath. On pouring the mixture into water there is obtained as product 4,5-bis(4-acetoxyphenyl)-2-(1,1,2,2-tetrafluoroethylsulfonyl)imidazole.

EXAMPLE 101

4,5-Diphenyl-2-trifluoromethylthioimidazole

A mixture of 27 g (0.122 mole) 4,5-diphenylimidazole, 21 g (0.25 mole) dihydropyran, 250 ml ethyl acetate and 4.0 g $BF_3 \cdot Et_2O$ was refluxed for five days. The nearly clear solution was diluted with ether and filtered to remove 0.6 g insoluble starting material. The ether filtrate was washed several times with 10% $NaHCO_3$ then dried and evaporated. TLC showed starting material still present, so the crude product was chromatographed on 2 lb SilicAR CC-7, eluting with toluene containing 20 to 40% ethyl acetate. The pure 4,5-diphenyl-1-(2-tetrahydropyranyl)imidazole thus obtained weighed 30.3 g (82%) and had m.p. 170°-171°.

Anal. Calc'd for $C_{20}H_{20}N_2O$: C, 78.92; H, 6.62; N, 9.20 Found: C, 78.57; H, 6.89; N, 9.07.

Under nitrogen and in glassware dried with a heat gun, a solution of 0.9 g (3 mmole) of 4,5-diphenyl-1-(2-tetrahydropyranyl)imidazole in 15 ml THF and 15 ml ether was chilled to −78° C. To the cold solution was added dropwise a solution of 2.5 ml (4 mmole) of 1.6 M n-butyl lithium in hexane in 10 ml ether. The solution was stirred at −78° C., then 0.55 g (4 mmole) of trifluoromethanesulfenyl chloride (TOXIC) was added as a gas. The mixture was stirred at −78° C. for 2 hours, then at RT overnight. The mixture was poured into water and extracted with ether (pH of aqueous layer ~4). The aqueous layer was neutralized with bicarbonate then extracted with more ether. The combined ether extracts were dried and concentrated. The crude residue was chromatographed on 50 g SilicAR CC-7, eluting with 98% toluene/2% ethyl acetate, to give 0.45 g (47%) of product. Recrystallization from toluene gave 0.3 g (31%) of white solid, mp 254°-6°.; Anal. Calc'd. for $C_{16}H_{11}F_3N_2S$: C, 59.99; H, 3.46; N, 8.75. Found: C, 60.20; H, 3,57; N, 8.52.

EXAMPLE 102

4,5-bis(4-(Fluorophenyl)-2-trifluoromethylthioimidazole

Using the procedures of Example 101, and substituting 4,5-bis(4-fluorophenyl)imidazole for the 4,5-diphenylimidazole of Example 101, one obtains as final product 4,5-bis(4-fluorophenyl)-2-trifluoromethylthioimidazole, mp 228°-229° C.

Anal. Calc'd. for $C_{16}H_9F_5N_2S$: C, 53.93; H, 2.55; N, 7.86. Found: C, 54.17, 54.12; H, 2.59, 2.58; N, 7.34, 7.97.

EXAMPLE 105

4,5-Diphenyl-2-(1,1,2,2-tetrafluoroethylthio)imidazole Hydrochloride

A solution of 5.0 g of 4,5-diphenyl-2-(1,1,2,2-tetrafluoroethylthio)imidazole (Example 18) in a mixture of ether and tetrahydrofuran was treated with dry hydrogen chloride gas and a precipitate was collected by filtration to give 4.7 g of 4,5-diphenyl-2-(1,1,2,2-tetrafluoroethylthio)imidazole hydrochloride, m.p. 192°-202°.

Anal. Calc'd. for $C_{17}H_{12}F_4N_2SHCl$: C, 52.51; H, 3.34; N, 7.21. Found: C, 52.06; H, 3.39; N, 7.25.

For additional chemical examples see Tables I, II, and III.

Using the appropriate starting materials and the procedure described in the above examples, the compounds in Table I can be prepared.

Using the appropriate starting materials and the procedure described in Example 18, the compounds in Table II can be prepared. Typical catalysts that can be used are diisopropylamine or benzyl trimethylammonium hydroxide.

Using the appropriate starting materials and the procedures described in Examples 13 and 14, the compounds in Table III can be prepared.

Table IV shows other compounds that can be prepared using the procedures described in the Examples.

Dosage Forms

The anti-arthritic agents and analgesic agents of this invention can be administered to treat arthritis or alleviate pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.001 to 40 milligrams per kilogram of body weight. Ordinarily 0.005 to 20, and preferably 0.01 to 4 milligrams per kilogram per day given in divided doses 2 to 4 times a day or in sustained release form is effective to obtain desired results.

Dosage forms (compositions) suitable for internal administration contain from about 0.1 milligrams to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours.

Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 10 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

Injectable

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

Use

To detect and compare the anti-inflammatory and immunoregulatory activities of compounds in this series and standard drugs, a series of tests was used based on a standard model for which there is good correlation with human efficacy. The model is adjuvant-induced arthritis in rats. Federation Proceedings, Vol. 32, No. 2, 1973

"Models Used for the Study and Therapy of Rheumatoid Arthritis"—Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

Established Adjuvant-Induces Arthritis in Rats

A test used primarily to determine anti-inflammatory activity.

Charles River Lewis male rats (130–150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant injected rats are culled and distributed to treatment groups of 10 of equal disease severity. Non-arthritic controls are distributed to 2 groups of 10. The rats are given oral doses of compound or PVA-Acacia* (10 ml/kg) by gavage on that day and on the 6 following days. One day after the last dose the paw volumes (uninjected, left hind paw) are measured using a Ugo Basile Volume Differential Meter Model 7101. 6 *Polyvinyl Alcohol 1%, Gum Acacia, U.S.P. 5%, Methylparaben 0.5%.

| Arthritic Control Mean Paw Volume (ml) | Treatment Group Mean Paw Volume (ml) |
|---|---|
| Arthritic Control Mean Paw Volume (ml) | Non-Arthritic Control × 100 = Mean Paw Volume (ml) |
| % Decrease from Control Mean Paw Volume. | |

Dose-response regression lines of the % decrease are plotted on semi-log paper by visual fit and the ED50% decrease from control paw volume is determined by inspection.

Data from the established adjuvant-induced arthritis test for the compounds of this invention are included in Tables I, II, and III.

Non-Established Adjuvant-Induces Arthritis in Rats

A test used primarily to determine the effects of compounds on the immunological reactions involved in the induction process and to prevent the development of arthritis.

Charles River Lewis male rats (130–150 grams) are injected subcutaneously in the plantar area of the right hind paw with 0.1 ml of adjuvant (Difco heat-killed, lyophilized *Mycobacterium butyricum* suspended in mineral oil 5 mg/ml). 40 Non-arthritic controls are injected with mineral oil. Groups of 20 rats are given single, daily oral doses of compound (in PVA-Acacia vehicle, 10 ml/kg) or vehicle by gavage beginning immediately following paw injection for a total of 14 doses. The paw volume of the uninjected (left) hind paw is measured 24 hours after the last dose using a Ugo Basile Volume differential meter Model 7101. The ED50% decrease from control is determined as described above.

To further evaluate the immunoregulatory properties of these compounds, two additional tests were used that are described below. The Jerne Hemolytic Plaque Assay measures the effect of compounds on specific antibody producing cells (B lymphocytes). The relative proportion of B lymphocytes and T lymphocytes (involved in cell mediated immunity) is determined by fluorescent antibody staining.

MODIFIED JERNE SPLEEN CELL HEMOLYTIC PLAQUE ASSAY

METHODS

A modification of the technique described by N. K. Jerne and A. A. Nordin (Science, 140, 450, 1963) was used in these studies. Rats (Charles River Lewis) with adjuvant-induced arthritis (and non-arthritic controls) were dosed orally ounce per day with PVA-Acacia vehicle* or compounds in vehicle from day 14 (following adjuvant injection) to day 20. The animals were sensitized with sheep red blood cells (SRBC) (0.2 ml of a 10% suspension = $2-3 \times 10^6$ cells) I.V. on day 17. The SRBC (Microbiological Associates) were washed 3 times in 0.9% sodium chloride solution prior to injection. On day 21 the rats were anesthetized with 1% sodium pentobarbital I.P. and the spleens were removed. Each spleen was placed on a stainless steel screen suspended over a plastic beaker in an ice bath and gently macerated with a glass syringe plunger. The cells were washed through the mesh into the beaker using a pasteur pipette to apply about 10 ml of Eagle's Minimal Essential Medium (MEM) during the maceration process until only fibrous material remained on the screen. Large particles were allowed to settle out for about 5 minutes and about 5 ml of supernatant was transferred to a plastic tube. Dilutions of 1:10 and 1:20 were made in cold MEM.
*Polyvinyl Alcohol 1%, Gum Acacia, 5%, Methylparaben 0.5% in water.

Plating: 2 ml of 0.7% Agarose (1.4% diluted 1:2 with 2X Eagles MEM) and 0.2 ml of a 10% SRBC suspension were pre-warmed in a 45° C. water bath. 20 Lambda of spleen cell dilution were added, mixed gently and poured into a supporting layer of 2 ml of 1.4% Agarose in a 60×15 mm plastic petri plate. Plates were incubated at 37° C. for 1.5 hours in a humidified incubator. 1.5 ml of guinea pig complement (diluted 1:10 with MEM) was added and incubation was continued for 1 hour longer.

Zones of hemolysis (plaques) per plate were counted without magnification against a diffuse light source. Assuming each plaque to have resulted from hemolysin produced by a single spleen cell, the number of plaque forming cells (PFC) per million spleen cells was calculated for each dilution. The statistical calculations (mean, standard error and "t" test) included the PFC/million count for each dilution of each spleen.

IMMUNOFLUORESCENT ANTIBODY STAINING OF B-CELLS IN RAT SPLEEN

METHOD

For the % B-cell ratio determinations rats (Charles River Lewis strain) in the process of developing adjuvant arthritis were used. Rats were dosed orally once a day with PVA-Acacia* vehicle or drug in vehicle. Treatment was started on day -3 pre-adjuvant. On day 0 rats were injected subcutaneously into the left hind paw with 0.1 ml (5 mg/ml) *Mycobacterium butyricum* (Difco-dried, heat-killed) in mineral oil. Drug treatment was continued through day 7. Spleens were harvested on day 8 post-adjuvant.
*Polyvinyl Alcohol 1%, Gum Acacia 5%, Methylparaben 0.5% in water.

Spleen cell suspension were prepared by macerating spleens on stainless steel sieve into medium RPMI 1640.

Large particles were allowed to settle and the supernatant was transferred to clean tubes and spun at 800 rmp IEC International Centrifuge Model K Size 2 for 10 minutes. The cell button was resuspended in 0.83% NH4Cl (pH adjusted to 7.0 with NaOH) for lysis of red cells (approximately 1 part packed cells to 3 parts NH4Cl). These suspensions were kept in ice for 5-7 minutes then spun at 800 rpm for 10 minutes. Cells were washed twice in Dulbecco's Phosphate Buffered Saline (PBS) and finally suspended in Dulbecco's PBS. The final cell concentration was such that one drop of cell suspension on a microscope slide covered with a coverslip gave 10-15 cells per high power field. Judging the size of the cell button and from experience 8-10 ml of Dulbecco's PBS per spleen were added to this final cell suspension.

For immunofluorescent staining, 0.2 ml of cell suspension was mixed with 0.2 ml of a 1:4 dilution of Fluorescein Isothiocyanate conjugated Rabbit-Anti-Rat IgG (Miles-Yeda Laboratories). Cells were incubated at 20° –4° C. for 1 hour, spun at 800 rpm for 10 minutes, washed twice in 2 ml of Dulbecco's PBS and resuspended in 0.2 ml of Dulbecco's PBS. One drop of cell suspension was placed on a microscope slide, covered with a coverslide and examined by light and fluorescence microscopy. A total of 200-300 cells was counted per spleen suspension. The number of fluorescing lymphocytes or B-cells was expressed as percent.

Data pertaining to the effects of some compounds from this series in the tests described above are summarized in Tables V, VI and VII.

Some of the compounds of this invention were equipotent in the treatment of established arthritis in rats (anti-inflammatory effect) and in preventing the development of arthritis in rats (non-established arthritis) as shown in Table V. Standard anti-inflammatory drugs such as indomethacin and phenylbutazone were less effective in preventing the development of arthritis in rats than in treating the inflammation in established arthritis. An immunosuppressive drug, cyclophosphamide, was more effective in preventing the development of arthritis in rats than in treating established arthritis in rats. Some of the compounds of this series demonstrated unique properties in these tests.

Rats with adjuvant-induced arthritis have greatly modified immunological systems as indicated by the increased number of plaque forming (antibody producing) cells (PFC) in spleen cell suspensions (hemolytic plaque assay Table VI). Treatment of arthritic rats with compounds of this invention reduced the number of PFC toward normal. Treatment with indomethacin had no effect on the number of PFC while treatment with cyclophosphamide reduced the PFC far below normal. Certain compounds of this series produced unique activity in this test.

Spleen cell suspensions from rats with adjuvant-induced arthritis have a larger proportion of B (antibody producing) lymphocytes than T lymphocytes (mediators of cellular immunity) when compared to cells from normal rats (Table VII). Treatment of arthritic rats with certain compounds of this invention reduced the B lymphocyte proportion to normal. Treatment with indomethacin had no effect on the lymphocyte population while treatment with cyclophosphamide reduced the B lymphocyte proportion to below normal.

Phenylquinone Writhing Test

A standard procedure for detecting and comparing the analgesic activity of compounds in this series for which there is good correlation with human efficacy is the standard phenylquinone writhing test modified from Siegmund, et al., *Proc. Soc. Exp. Biol. Med.* 95, 729 (1957). A test compound suspended in 1% methylcellulose was given orally to fasted (17-21 hours) female white mice, 5-20 animals per double blind test. Aqueous (0.01% phenyl-p-benzoquinone) phenylquinone was injected intraperitoneally at 24 minutes later using 0.20 ml per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.* 11, 115-145 (1947); also time of peak action was determined for many of the compounds. This data is summarized in Tables VIII and IX.

Table I 4,5-Diaryl-2-(substituted-thio)imidazoles and their Rat Adjuvant Arthritis[1] Data

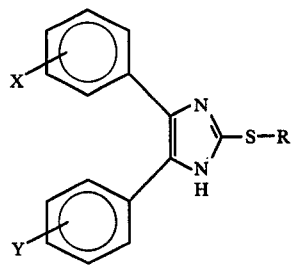

| Example | X | Y | R | m.p. | Adjuvant Arthritis ($ED_{50\%}$)[2,5] |
|---|---|---|---|---|---|
| 15 | 4-CH3O | 4-CH3O | CH3 | 156°-157° | 4.4 |
| 26 | 4-Cl | 4-Cl | CH3 | 241°-242° | 3.0 |
| 27 | 4-CH3O | 4-CH3O | CH3CH2CH2 | 152°-153° | 9.0 |
| 28 | 4-F | 4-F | CH3 | 222°-223.5° | 3.5 |
| 29 | 4-CH3O | 4-CH3O | CHF2 | 170.5°-172° | 1.8 |

Table I-continued
4,5-Diaryl-2-(substituted-thio)imidazoles and their Rat Adjuvant Arthritis[1] Data

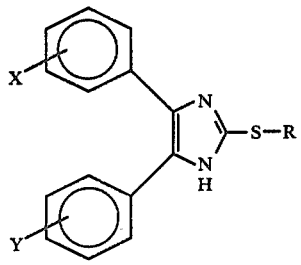

| Example | X | Y | R | m.p. | Adjuvant Arthritis $(ED_{50\%})^{2,5}$ |
|---|---|---|---|---|---|
| 30 | H | H | $CHF_2$ | 227°–228° | 21 |
| 31 | 4-Cl | 4-Cl | $CHF_2$ | 222°–223° | 0.35 |
| 32 | 4-F | 4-F | $CHF_2$ | 192.5°–194° | 0.42 |
| 33 | 4-Cl | 4-F | $CH_3$ | 222°–223° | 3.8 |
| 34 | 4-$CF_3$ | H | $CH_3$ | 176°–177° | 20 |
| 35 | 4-F | 4-$CF_3$ | $CH_3$ | 196°–197° | 17 |
| 36 | 4-Cl | 4-$CF_3$ | $CH_3$ | 214°–215° | 3.6 |
| 37 | 3,4-$OCH_2O$ | 3,4-$OCH_2O$ | $CH_3$ | 201°–202° | 20 |
| 4 | 4-$CH_3O$ | 4-$CH_3O$ | $CF_3CH_2$ | 150°–151°[3] | 20 |
| 7 | 4-Cl | 4-Cl | $CF_3CH_2$ | 212°–213° | 5.0 |
| 10 | 4-$CH_3O$ | 4-$CH_3O$ | $CH_3CH_2$ | 108°–109°[4] | 4.7 |
| 11 | 4-$CH_3$ | 4-$CH_3O$ | $CH_2=CHCH_2$ | 167°–167.5° | 22 |
| 16 | 4-$CH_3O$ | 4-$CH_3O$ | $CH_3COCH_2$ | 115°–117.5° | 9.4 |
| 17 | 4-$CH_3O$ | 4-$CH_3O$ | $CH_3SOCH_2$ | 84.5°–86.5° | 52 |
| 106 | 4-$CH_3O$ | 4-$CH_3O$ | $CHBr_2CF_2$ | 172°–174° | 23 |
| 107 | 4-$CH_3O$ | 4-$CH_3O$ | $CF_3$ | 181°–182° | 1.5 |
| 108 | 4-F | 4-F | $CH_3CH_2CH_2CH_2$ | 175°–175.5° | (77%/10) |
| 109 | 4-$CH_3O$ | 4-F | $CF_3$ | 156°–157.5° | 2.7 |
| 110 | 4-F | 4-F | $CF_3CF_2$ | 235°–237° | 0.2 |
| 111 | H | 3,4-$Cl_2$ | $CF_3$ | 241°–242° | 7 |
| 112 | H | 3,4-$Cl_2$ | $CH_3$ | 183.5°–184.5° | (62%/25) |
| 113 | H | 3-F | $CH_3$ | 202°–203° | 50 |
| 114 | H | 3-Cl | $CH_3$ | 171°–172° | (45%/50) |
| 115 | H | 4-$OC_2H_5$ | $CH_3$ | 184°–185° | (33%/50) |

[1]This biological system is described previously.
[2]Units are in mg./kg.
[3]A polymorph had m.p. 119°–120°
[4]A polymorph had m.p. 146°
[5]$ED_{50}$ values in parenthesis represent the percent (%) reduction in paw volume measured at the indicated dose (mg./kg.)

Table II
4,5-Diaryl-2-(polyhaloalkylthio)imidazoles and their Rat Adjuvant Arthritis[1] Data

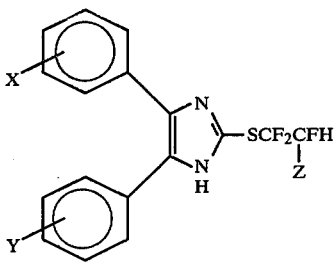

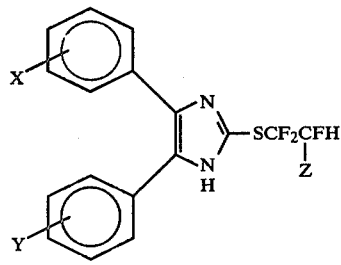

| Ex. | X | Y | Z | m.p. | Adjuvant Arthritis $(ED_{50\%})^{2,3}$ |
|---|---|---|---|---|---|
| 38 | 4-$CH_3O$ | 4-$CH_3O$ | F | 134°–136° | 4.2 |
| 39 | 4-Cl | 4-Cl | F | 222.5°–223.5° | 0.3 |
| 40 | 4-F | 4-F | F | 220°–221.5° | 0.075 |
| 41 | H | H | Cl | 187°–188° | 3.9 |
| 42 | 4-Cl | 4-F | F | 206.5°–207.5° | 0.18 |
| 43 | 4-$CH_3$ | 4-$CH_3$ | F | 204°–205° | 18 |
| 44 | 4-$CH_3O$ | H | F | 175°–175.5° | 20 |
| 45 | 4-Cl | H | F | 205°–206° | 0.3 |
| 46 | 3,4-$OCH_2O$ | 3,4-$OCH_2O$ | F | 204°–205.5° | 10 |
| 47 | 4-$CF_3$ | H | F | 202°–205° | 4.5 |
| 48 | 4-F | 4-$CF_3$ | F | 182.5°–183.5° | 1.5 |
| 49 | 4-F | H | F | 196°–197.5° | 0.2 |
| 50 | 2-Cl | 3-Cl | F | 208°–209° | 1.2 |
| 51 | 4-$CH_3O$ | 4-$CH_3O$ | Br | 151°–153° | 10 |

Table II-continued
4,5-Diaryl-2-(polyhaloalkylthio)imidazoles and their Rat Adjuvant Arthritis[1] Data

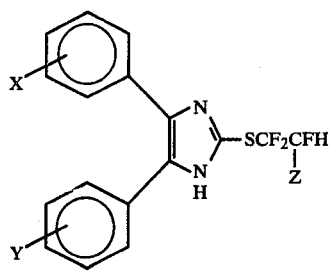

| Ex. | X | Y | Z | m.p. | Adjuvant Arthritis (ED$_{50\%}$)[2,3] |
|---|---|---|---|---|---|
| 52 | H | H | Br | 184°–186° | 11 |
| 53 | 4-(CH$_3$)$_2$N | H | F | 189°–192.5° | 2.5 |
| 18 | H | H | F | 218°–219.5° | 0.75 |
| 116 | 4-CH$_3$O | 4-CH$_3$O | I | 183°–184° | 30 |
| 117 | 4-F | 4-CH$_3$O | F | 170°–171.5° | 14 |
| 118 | H | 4-C$_2$H$_5$O | F | 185°–186° | (32%/10) |
| 119 | H | 3,4-Cl | F | 209°–211° | 3.0 |
| 120 | H | 3-F | F | 205.5°–207° | (37%/1.0) |
| 121 | H | 3-Cl | F | 212°–213° | 0.6 |
| 122 | H | 4-N(CH$_3$)$_2$ | F | 189°–192.5° | 4.0 |

[1]This biological system is described previously.
[2]Units are in mg./kg.
[3]ED$_{50}$ values in parenthesis represent the percent (%) reduction in paw volume measured at the indicated dose (mg./kg.)

Table III
4,5-Diaryl-2-(alkylsulfinyl)imidazoles and 4,5-Diaryl-2-(alkylsulfonyl)imidazoles and their Rat Adjuvant Arthritis[1] Data

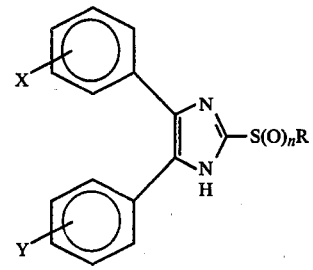

| Example | X | Y | R | n | m.p. | Adjuvant Arthritis (ED$_{50\%}$)[2,3] |
|---|---|---|---|---|---|---|
| 2 | H | H | CF$_3$CH$_2$ | 1 | 198° (dec.) | 48 |
| 3 | H | H | CF$_3$CH$_2$ | 2 | 226.5° (dec.) | 12 |
| 5 | 4-CH$_3$O | 4-CH$_3$O | CF$_3$CH$_2$ | 1 | 193.5° (dec.) | 10 |
| 6 | 4-CH$_3$O | 4-CH$_3$O | CF$_3$CH$_2$ | 2 | 173.5–174.5° | 3.8 |
| 8 | 4-Cl | 4-Cl | CF$_3$CH$_2$ | 1 | 214° (dec.) | 3.0 |
| 9 | 4-Cl | 4-Cl | CF$_3$CH$_2$ | 2 | 241° (dec.) | 4.5 |
| 13 | 4-CH$_3$O | 4-CH$_3$O | CH$_3$CH$_2$ | 1 | 161–162° | 10 |
| 14 | 4-CH$_3$O | 4-CH$_3$O | CH$_3$CH$_2$ | 2 | 136–137° | 5.2 |
| 54 | 4-CH$_3$O | 4-CH$_3$O | CH$_2$=CHCH$_2$ | 1 | 118–119° (dec.) | 11 |
| 55 | 4-CH$_3$O | 4-CH$_3$O | CH$_2$=CHCH$_2$ | 2 | 162–163° | 11 |
| 56 | 4-CH$_3$O | 4-CH$_3$O | CH$_3$ | 1 | 167–168.5° | 6.2 |
| 57 | 4-CH$_3$O | 4-CH$_3$O | CH$_3$ | 2 | 142–143° | 6.4 |
| 58 | 4-Cl | 4-Cl | CF$_3$CH$_2$ | 1 | 214° (dec.) | 3.0 |
| 59 | 4-Cl | 4-Cl | CH$_3$ | 1 | 202° (dec.) | 2.3 |
| 60 | H | H | HCF$_2$CF$_2$ | 2 | 239–240° | 0.13 |
| 61 | 4-CH$_3$O | 4-CH$_3$O | CH$_3$CH$_2$CH$_2$ | 1 | 143–144.5° | 13 |
| 62 | 4-CH$_3$O | 4-CH$_3$O | CH$_3$(CH$_2$)$_2$ | 2 | 152–153° | 9 |
| 63 | 4-CH$_3$O | 4-CH$_3$O | (CH$_3$)$_2$CH | 2 | 175–176° | 30 |
| 64 | 4-CH$_3$O | 4-CH$_3$O | HCF$_2$CF$_2$ | 2 | 156–157° | 1.1 |
| 65 | 4-CH$_3$O | 4-CH$_3$O | HCF$_2$CF$_2$ | 1 | 162.5–163.5° | 2.4 |
| 66 | H | H | HCF$_2$CF$_2$ | 1 | 181–182° | 0.18 |
| 67 | 4-Cl | 4-Cl | CH$_3$ | 2 | 255–256° | 2.0 |
| 68 | 4-Cl | 4-Cl | HCF$_2$CF$_2$ | 1 | 198° (dec.) | 0.2 |
| 69 | 4-Cl | 4-Cl | HCF$_2$CF$_2$ | 2 | 235–236.5° | 0.2 |
| 70 | 4-F | 4-F | CF$_3$CH$_2$ | 2 | 247° (dec.) | 3.5 |
| 71 | 4-F | 4-F | HCF$_2$CF$_2$ | 2 | 241.5–242° | 0.025 |
| 72 | 4-F | 4-F | CH$_3$ | 2 | 239–240° | 4.5 |
| 73 | H | H | ClFCHCF$_2$ | 2 | 213–214° | 0.25 |
| 74 | 4-CH$_3$O | 4-CH$_3$O | CHF$_2$ | 2 | 186–187° | 0.5 |
| 75 | H | H | CHF$_2$ | 2 | 265° | 0.35 |
| 76 | H | H | HCCl$_2$CF$_2$ | 2 | 223–223.5° | 1.5 |
| 77 | 4-Cl | 4-Cl | CHF$_2$ | 2 | 244–245° | 0.35 |
| 78 | 4-F | 4-F | CHF$_2$ | 2 | 246.5–247° | 0.1 |
| 79 | 4-Cl | 4-F | CH$_3$ | 2 | 226–227° | 2.8 |
| 80 | 4-Cl | 4-F | HCF$_2$CF$_2$ | 2 | 212–213° | 0.09 |
| 81 | 4-CH$_3$ | 4-CH$_3$ | HCF$_2$CF$_2$ | 2 | 225–226° | 0.35 |
| 82 | 4-CH$_3$O | H | HCF$_2$CF$_2$ | 2 | 169–170° | 1.1 |
| 83 | 2-Cl | 4-CH$_3$O | HCF$_2$CF$_2$ | 2 | 176–177° | 7.2 |
| 84 | 3-CH$_3$O | 3-CH$_3$O | HCF$_2$CF$_2$ | 2 | 155.5–156.5° | 4.0 |
| 85 | 4-Cl | H | CH$_3$ | 2 | 169–170° | 30 |
| 86 | 4-Cl | H | HCF$_2$CF$_2$ | 2 | 206–207.5° | 0.065 |
| 87 | 4-F | 4-CF$_3$ | CH$_3$ | 2 | 189–190° | 3.7 |

Table III-continued
4,5-Diaryl-2-(alkylsulfinyl)imidazoles and 4,5-Diaryl-2-(alkylsulfonyl)imidazoles and their Rat Adjuvant Arthritis[1] Data

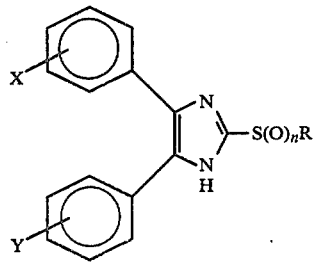

| Example | X | Y | R | n | m.p. | Adjuvant Arthritis (ED$_{50\%}$)[2,3] |
|---|---|---|---|---|---|---|
| 88 | 4-Cl | 4-CF$_3$ | CH$_3$ | 2 | 224–225° | 2.2 |
| 89 | 4-CF$_3$ | H | HCF$_2$CF$_2$ | 2 | 188–189° | 2.4 |
| 90 | 4-Cl | 4-CF$_3$ | HCF$_2$CF$_2$ | 2 | 208–209° | 1.8 |
| 91 | 2-Cl | 2-Cl | HCF$_2$CF$_2$ | 2 | 183–184° | 0.8 |
| 92 | 4-F | H | HCF$_2$CF$_2$ | 2 | 228–229° | 0.027 |
| 93 | 3-Cl | 3-Cl | HCF$_2$CF$_2$ | 2 | 208–209° | 0.16 |
| 94 | 4-Cl | 4-Cl | CHF$_2$ | 1 | 203–206 | 0.19 |
| 95 | 4-CH$_3$O | 4-CH$_3$O | BrFCHCF$_2$ | 2 | 187–188° | 2.4 |
| 96 | 4-CH$_3$ | H | HCF$_2$CF$_2$ | 2 | 202–203° | 0.6 |
| 97 | 3,4-OCH$_2$O | 3,4-OCH$_2$O | HCF$_2$CF$_2$ | 2 | 212–214° | 1.0 |
| 17 | 4-CH$_3$O | 4-CH$_3$O | CH$_3$SCH$_2$ | 1 | 142.5–143.5° | 28 |
| 98 | 4-CH$_3$O | 4-CH$_3$O | CH$_3$COCH$_2$ | 1 | 138–140° | 56 |
| 99 | 4-CH$_3$O | 4-CH$_3$O | CH$_3$SO$_2$CH$_2$ | 2 | 202–203° | 54 |
| 100 | 4-CH$_3$O | 4-CH$_3$O | CH$_3$COCH$_2$ | 2 | 134–135° | 18 |
| 103 | H | H | CF$_3$ | 2 | 292–293.5° | 0.03 |
| 104 | 4-F | 4-F | CF$_3$ | 2 | 264–265° | 0.015 |
| 124 | H | H | H$_2$CFCF$_2$ | 2 | 239–240° | 0.15 |
| 125 | 4-CH$_3$O | 4-CH$_3$O | H$_2$CFCF$_2$ | 2 | 162–164° | 5 |
| 126 | H | H | HCBrFCF$_2$ | 2 | 217–218° | 0.85 |
| 127 | 4-CH$_3$O | 4-CH$_3$O | CF$_3$ | 2 | 201–202.5° | 0.33 |
| 128 | 4-CH$_3$O | 4-CH$_3$O | HCFICF$_2$ | 2 | 190–192° | 3 |
| 129 | 4-CH$_3$O | 4-CH$_3$O | CH$_3$CH$_2$CH$_2$CH$_2$ | 2 | 99–101° | (71%/50) |
| 130 | 4-CH$_3$O | 4-F | CF$_3$ | 2 | 187–188° | 1.4 |
| 131 | 4-Cl | 4-CH$_3$ | HCF$_2$CF$_2$ | 2 | 220–220.5° | (36%/10) |
| 132 | H | 3,4-Cl$_2$ | CF$_2$ | 2 | 195.5–197° | 0.5 |
| 133 | 4-F | 4-CH$_3$O | HCF$_2$CF$_2$ | 2 | 189–190° | 2.2 |
| 134 | 4-F | 4-F | HCF$_2$CF$_2$ | 1 | 192.5–193° | 0.055 |
| 135 | 4-NO$_2$ | 4-NO$_2$ | HCF$_2$CF$_2$ | 2 | 240–240.5° | 8.5 |
| 136 | 4-F | 4-F | CH$_3$ | 1 | 185–187° | 4 |
| 137 | H | 3,4-Cl$_2$ | HCF$_2$CF$_2$ | 2 | 197–198° | 0.25 |
| 138 | H | 4-C$_2$H$_5$O | CH$_3$ | 2 | 172.5–173.5° | (41%/50) |
| 139 | H | 3-Cl | CH$_3$ | 1 | 150–151.5° | (77%/75) |
| 140 | 3-Cl | 3-Cl | HCF$_2$CF$_2$ | 2 | 208–209° | 0.16 |
| 141 | H | 4-F | CH$_3$ | 2 | 215–216° | (26%/9) |
| 142 | H | 4-C$_2$H$_5$O | HCF$_2$CF$_2$ | 2 | 162–163° | 1.5 |
| 143 | H | 3-F | HCF$_2$CF$_2$ | 2 | 217–218° | 0.06 |
| 144 | H | 3-Cl | HCF$_2$CF$_2$ | 2 | 193–194° | 0.05 |
| 145 | H | 3,4-Cl$_2$ | CH$_3$ | 2 | 199–200° | (59%/50) |
| 146 | H | 3,4-Cl$_2$ | CH$_3$ | 1 | 188–189° | 50 |
| 147 | H | 3-F | CH$_3$ | 2 | 215–216° | (32%/75) |
| 148 | H | 3-F | CH$_3$ | 1 | 163.5–164.5° | (67%/100) |
| 149 | H | 3-Cl | CH$_3$ | 2 | 171–172° | (55%/10) |

[1]This biological system is described previously.
[2]Units are in mg./kg.
[3]ED$_{50}$ values in parenthesis represent the percent (%) reduction in paw volume measured at the indicated dose (mg./kg.)

Table IV

Structure: diphenyl imidazole with X on one phenyl, Y on other, 2-S(O)$_n$R substituent on imidazole NH

| X | Y | R | n |
|---|---|---|---|
| 3-Cl | H | HCF$_2$CF$_2$ | 1 |
| 2-Cl | 2-Cl | HCF$_2$CF$_2$ | 2 |
| 4-n-C$_4$H$_9$ | 4-n-C$_4$H$_9$ | HCF$_2$CF$_2$ | 2 |
| 4-C$_2$H$_5$O | 4-C$_2$H$_5$O | HCF$_2$CF$_2$ | 0 |
| 4-N(CH$_3$)$_2$ | 4-N(CH$_3$)$_2$ | HCF$_2$CF$_2$ | 0 |
| 4-NO$_2$ | H | HCF$_2$CF$_2$ | 2 |
| 4-CH$_3$S | 4-CH$_3$S | HCF$_2$CF$_2$ | 0 |
| 4-CH$_3$SO$_2$ | 4-CH$_3$SO$_2$ | HCF$_2$CF$_2$ | 2 |
| 4-t-C$_4$H$_9$O | 4-t-C$_4$H$_9$O | HCF$_2$CF$_2$ | 2 |
| 4-F | 4-F | H$_2$CFCF$_2$ | 2 |

TABLE V

ADJUVANT-INDUCED ARTHRITIS IN RATS

| CHEMICAL EXAMPLE NUMBER | ED50% mg/kg ESTABLISHED ARTHRITIS | NON-ESTABLISHED ARTHRITIS |
|---|---|---|
| 18 | 0.75 | 2.3 |
| 39 | 0.2 | 0.06 |
| 71 | 0.03 | 0.03 |
| Phenylbutazone | 10 | 35 |
| Indomethacin | 0.3 | 3 |
| Cyclophosphamide | 10 | 1.5 |

TABLE VI

HEMOLYTIC PLAQUE ASSAY IN SPLEEN CELL SUSPENSIONS FROM ARTHRITIC, NON-ARTHRITIC AND DRUG TREATED ARTHRITIC RATS

| CHEMICAL EXAMPLE NUMBER | DAILY ORAL DOSE mg/kg | MEAN PLAQUE FORMING CELLS PER MILLION SPLEEN CELLS (N = 20) |
|---|---|---|
| 18 | 1.5 | 197 |
|  | 15 | 320 |
| 39 | 0.1 | 788 |
|  | 1.0 | 488 |
| 71 | 0.03 | 499 |
|  | 0.3 | 439 |
| 86 | 0.07 | 412 |
|  | 0.7 | 367 |
| Arthritic Control* | — | 787 |
| Non-Arthritic Control* | — | 323 |
| Indomethacin** | 1.0 | 694 |
| Cyclophosphamide | 5.0 | 25 |

*Data pooled from 4 experiments.
**Data pooled from 3 experiments.

TABLE VII

PROPORTION OF B LYMPHOCYTES IN SPLEEN CELL SUSPENSIONS FROM ARTHRITIC, NON-ARTHRITIC AND DRUG TREATED ARTHRITIC RATS AS DETERMINED BY FLUORESCENT ANTIBODY STAINING

| CHEMICAL EXAMPLE NUMBER | DAILY ORAL DOSE mg/kg | MEAN % B CELLS |
|---|---|---|
| 18** | 1.5 | 37 |
|  | 15 | 34 |
| 39** | 0.2 | 37 |
|  | 2.0 | 35 |
| 71*** | 0.03 | 38 |
|  | 0.3 | 41 |
| 86 | 0.1 | 48 |
|  | 1.0 | 42 |
| Arthritic Control* | — | 56 |
| Non-Arthritic Control* | — | 41 |
| Phenylbutazone | 20 | 53 |
| Indomethacin | 0.5 | 57 |
| Cyclophosphamide | 5 | 25 |

*Pooled data from 8 experiments (N = 40).
**Pooled data from 2 experiments (N = 10).
***Pooled data from 3 experiments (N = 15).

TABLE VIII

Phenylquinone Writhing Test

Structure: 4,5-bis(4-methoxyphenyl)imidazole with 2-S(O)$_n$-R

| R | n | ED$_{50}$* | PEAK TIME (min) |
|---|---|---|---|
| CHF$_2$ | 2 | 1.5 | |
| CF$_3$ | 2 | 0.045 | 240 |
| CH$_2$CF$_3$ | 1 | 0.86 | 60 |
| CH$_2$CF$_3$ | 0 | 1.2 | 240 |
| CH$_2$CF$_3$ | 2 | 0.58 | 60 |
| CF$_2$CH$_2$F | 2 | 0.25 | 160 |
| CF$_2$CHF$_2$ | 1 | 0.8 | |
| CF$_2$CHF$_2$ | 2 | 0.11 | 120 |
| CF$_2$CHBrF | 2 | 2.8 | |

Phenylquinone Writhing Test

Structure: 4,5-diphenyl imidazole with X, Y substituents and 2-S(O)$_n$-R

| X | Y | R | n | ED$_{50}$* | PEAK TIME (min) |
|---|---|---|---|---|---|
| 4-CH$_3$O | 2-Cl | CF$_2$CHF$_2$ | 2 | 0.56 | 60 |
| 4-CH$_3$O | H | CF$_2$CHF$_2$ | 2 | 0.33 | 240 |
| 4-C$_2$H$_5$O | H | CF$_2$CHF$_2$ | 2 | 0.95 | 120 |
| H | H | CF$_2$CHF$_2$ | 2 | 0.48 | 120 |
| 4-CH$_3$O | 4-F | CF$_3$ | 2 | 0.1 | — |
| 4-F | 4-CH$_3$O | HCF$_2$CHF$_2$ | 2 | 0.27 | — |

*units are mg/kg

We claim:

1. A compound of the formula

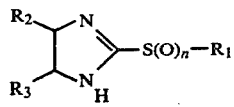

where
n=0, 1, or 2;
$R_1 = C_1-C_8$ alkyl; allyl; vinyl; $-CH_2COCH_3$; $-CH_2S(O)_m CH_3$, where m=0, 1, or 2; mono— or polyhalo— $C_1-C_8$ alkyl;
$R_2$ and $R_3$, the same or different=

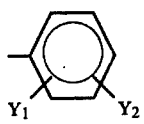

$Y_1$ and $Y_2$, the same or different=hydrogen, $C_1-C_4$ alkoxy, acetoxy, $C_1-C_4$ alkyl, Cl, F, $CF_3$, $N(CH_3)_2$, $NO_2$, $CH_3S—$, $CH_3SO_2—$, or $Y_1$ and $Y_2$ taken together forming a dioxymethylene bridge;
provided, when n=0, 1 or 2 and $Y_1$ and $Y_2$ both=hydrogen, $R_1$ cannot be vinyl;
provided, when $R_1 = C_1-C_8$ alkyl, $C_3-C_8$ haloalkyl with halogen substituted at the 3 through 8 position, allyl or $-CH_2COCH_3$, both $Y_1$ and $Y_2$ cannot be H;
provided further, when n=O and $R_1=CH_3$, both $Y_1$ and $Y_2$ cannot be p-Cl or p-$OCH_3$;
its pharmaceutically suitable acid addition salt where N=O or its pharmaceutically suitable metal salt where n=1 or 2.

2. A compound of claim 1 where
n=0, 1, or 2;
$R_1 = C_1-C_4$ alkyl; allyl; vinyl; $-CH_2COCH_3$; $-CH_2-S(O)_m CH_3$, where m=0, 1, or 2; mono— or polyhalo— $C_1-C_4$ alkyl;
$R_2$ and $R_3$, the same or different=

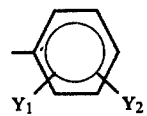

$Y_1$ and $Y_2$, the same or different= hydrogen, $C_1-C_4$ alkoxy, acetoxy, $C_1-C_4$ alkyl, Cl, F, $CF_3$, $-N(CH_3)_2$, $NO_2$, $CH_3S—$, $CH_3SO_2—$, or $Y_1$ and $Y_2$ taken together forming a dioxymethylene bridge;
provided when n=0, 1 or 2 and $Y_1$ and $Y_2$ both=hydrogen, $R_1$ cannot be vinyl provided, when $R_1=C_1-C_4$ alkyl, $C_3-C_4$ haloalkyl with halogen substituted at the 3 or 4 position, allyl, or $-CH_2COCH_3$, both $Y_1$ and $Y_2$ cannot be H;
provided further, when n=o and $R_1=CH_3$, both $Y_1$ and $Y_2$ cannot be p-Cl or p-$OCH_3$;
or its pharmaceutically suitable salt where n=1 or 2.

3. The compound of claim 1 where:
n=0, 1, or 2;
$R_1=C_1-C_4$ alkyl; allyl; $-CH_2COCH_3$; $-CH_2S(O)_m CH_3$, where m=0, 1, or 2; mono— and polyfluoro $C_1-C_4$ alkyl;
$R_2$ and $R_3$, the same or different=

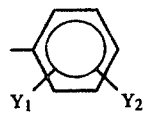

$Y_1$ and $Y_2$, the same or different=hydrogen, methoxy, ethoxy, acetoxy, $C_1-C_4$ alkyl, Cl, F, $CF_3$, $-N(CH_3)_2$, or $Y_1$ and $Y_2$ taken together forming a dioxymethylene bridge;
provided, when $R_1 = C_1-C_4$ alkyl, $C_3-C_4$ fluoroalkyl with the fluorine substituted at the 3 or 4 position, allyl, or $-CH_2COCH_3$, both $Y_1$ and $Y_2$ cannot be H;
provided further, when n=0 and $R_1=CH_3$, both $Y_1$ and $Y_2$ cannot be p-Cl or p-$OCH_3$.

4. The compound of claim 1 where $R_1=-CF_2CF_2H$.
5. The compound of claim 1 where $R_1=-CF_3$.
6. The compound of claim 1 where $R_2$ and $R_3$ independently, =

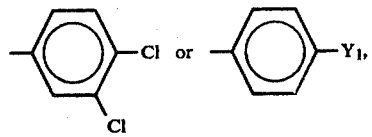

where $Y_1=H$, Cl, or F.

7. The compound of claim 1 where n=1 or 2.
8. The compound of claim 3 where
$R_1=-CF_2CF_2H$;
$R_2$ and $R_3$, independently, =

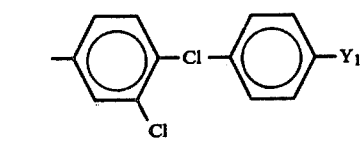

where
$Y_1=H$, Cl, or F; and
n=0, 1, or 2.

9. The compound of claim 3 where
$R_1=-CF_3$;
$R_2$ and $R_3$, independently, =

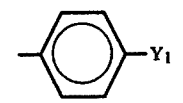

$Y_1=H$, Cl, or F; an
n=0, 1, or 2.

10. The compound of claim 3 where
$R_1=-CF_2CF_2H$;
$R_2$ and $R_3$, independently, =

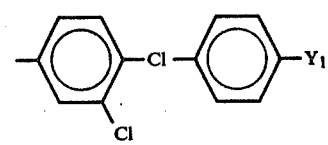

where $Y_1$=H, Cl, or F; and
n=0 or 2.

11. The compound of claim 3: 4(or 5)-(3,4-dichlorophenyl)-5(or 4)-phenyl-2-(1,1,2,2-tetrafluoroethylsulfonyl)imidazole.

12. The compound of claim 3: 4,5-bis(4-fluorophenyl)-2-(1,1,2,2-tetrafluoroethylsulfonyl)imidazole.

13. The compound of claim 3: 4(or 5)-(4-fluorophenyl)-5(or 4)-phenyl-2-(1,1,2,2-tetrafluoroethylsulfonyl)imidazole.

14. The compound of claim 3: 4,5-bis(4-chlorophenyl)-2-(1,1,2,2-tetrafluoroethylsulfonyl)imidazole.

15. The compound of claim 3: 4(or 5)-(4-chlorophenyl)-5(or 4)-phenyl-2-(1,1,2,2-tetrafluoroethylsulfonyl)imidazole.

16. The compound of claim 3: 4,5-diphenyl-2-(1,1,2,2-tetrafluoroethylsulfonyl)imidazole.

17. The compound of claim 3: 4,5-diphenyl-2-(1,1,2,2-tetrafluoroethylthio)imidazole.

18. The compound of claim 3: 4,5-diphenyl-2-trifluoromethylsulfonylimidazole.

19. The compound of claim 3: 4,5-bis(p-fluorophenyl)-2-trifluoromethylthioimidazole.

20. The compound of claim 3: 4,5-bis(p-fluorophenyl)-2-trifluoromethylsulfonylimidazole.

21. The compound of claim 3 of the formula

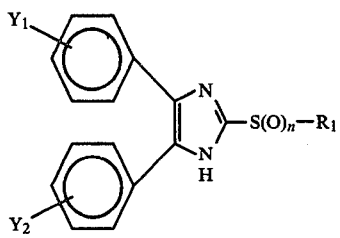

where
$R_1$=$C_1$-$C_4$ alkyl, monohalo- or polyhalo-$C_1$-$C_4$ alkyl;
$Y_1$ and $Y_2$, the same or different, =H, 2-methoxy, 4-methoxy, 2-ethoxy, 4-ethoxy, 2-chloro, or 4-chloro; and
n=0, 1, or 2.

22. The compound of claim 21 where
$R_1$=polyhalo-$C_1$-$C_2$ alkyl;
$Y_1$ and $Y_2$, the same or different=H, 2-methoxy, 4-methoxy, 2-ethoxy, 4-ethoxy, 2-chloro, or 4-chloro; provided, that at least one of $Y_1$ and $Y_2$=4-methoxy or 4-ethoxy; and
n=0, 1 or 2.

23. The compound of claim 22: 4,5-bis(4-methoxyphenyl)-2-(1,1,2-trifluoroethylsulfonyl)imidazole.

24. The compound of claim 22: 4,5-bis(4-methoxyphenyl)-2-(1,1,2,2-tetrafluoroethylsulfonyl)imidazole.

25. The compound of claim 22: 4,5-bis(4-methoxyphenyl)-2-(2,2,2-trifluoroethylthio)imidazole.

26. The compound of claim 22: 4,5-bis(4-methoxyphenyl)-2-(2,2,2-trifluoroethylsulfinyl)imidazole.

27. The compound of claim 22: 4,5-bis(4-methoxyphenyl)-2-(2,2,2-trifluoroethylsulfonyl)imidazole.

28. The compound of claim 22: 4,5-bis(4-methoxyphenyl)-2-(trifluoromethylsulfonyl)imidazole.

29. A pharmaceutical composition comprising a suitable pharmaceutical carrier and an effective antiarthritic amount of a compound of the formula

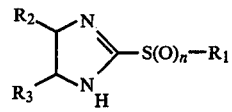

where
n=0, 1, or 2;
$R_1$=$C_1$-$C_8$ alkyl; allyl; vinyl; —CH$_2$COCH$_3$; —CH$_2$S(O)$_m$CH$_3$, where m=0, 1, or 2; mono- or polyhalo- $C_1$-$C_8$ alkyl;
$R_2$ and $R_3$, the same or different =

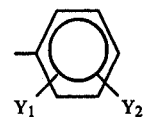

$Y_1$ and $Y_2$, the same or different=hydrogen, $C_1$-$C_4$ alkoxy, acetoxy, $C_1$-$C_4$ alkyl, Cl, F, CF$_3$, —N(CH$_3$)$_2$, NO$_2$, CH$_3$S, CH$_3$SO$_2$—, or $Y_1$ and $Y_2$ taken together forming a dioxymethylene bridge;
provided, when $R_1$=$C_1$-$C_8$ alkyl, $C_3$-$C_4$ haloalkyl with the halogen substituted at the 3 through 8 position, allyl, or —CH$_2$COCH$_3$ both $Y_1$ and $Y_2$ cannot be H;
its pharmaceutically suitable acid addition salt where n=0 or its pharmaceutically suitable metal salt where n=1 or 2.

30. The compound of claim 29 where
n=0, 1, or 2;
$R_1$=$C_1$-$C_4$ alkyl; allyl; —CH$_2$COCH$_3$; —CH$_2$S(O)$_m$CH$_3$, where m=0, 1, or 2; mono- or polyfluoro-$C_1$-$C_4$ alkyl;
$R_2$ and $R_3$, the same or different =

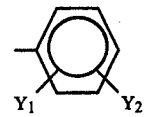

$Y_1$ and $Y_2$, the same or different=hydrogen, methoxy, ethoxy, acetoxy, $C_1$-$C_4$ alkyl, Cl, F, CF$_3$, —N(CH$_3$)$_2$, or $Y_1$ and $Y_2$ taken together forming a dioxymethylene bridge;
provided, when $R_1$=$C_1$-$C_4$ alkyl, $C_3$-$C_4$ fluoroalkyl with the fluorine substituted at the 3 or 4 position, allyl, or —CH$_2$COCH$_3$ both $Y_1$ and $Y_2$ cannot be H.

31. The compound of claim 29 wherein $R_1$=—CF$_2$CF$_2$H.

32. The compound of claim 29 where $R_1$=—CF$_3$.

33. The composition of claim 29 where $R_2$ and $R_3$ independently=

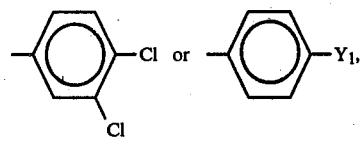

where $Y_1$=H, Cl, or F.

34. The compound of claim 29 where n=1 or 2.

35. The composition of claim 30 where $R_1 = -CF_2CF_2H$;
$R_2$ and $R_3$, independently, =

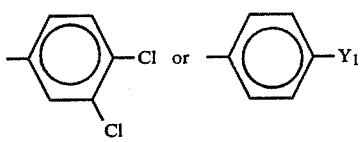

where
$Y_1 = H$, Cl, or F; and
n = 0, 1, or 2.

36. The composition of claim 30 where
$R_1 = -CF_3$;
$R_2$ and $R_3$, independently, =

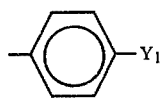

where
$Y_1 = H$, Cl, or F; and
n = 0, 1, or 2.

37. The composition of claim 30 where
$R_1 = -CF_2CF_2H$:
$R_2$ and $R_3$, independently, =

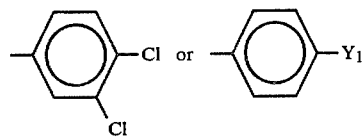

where
$Y_1 = H$, Cl, or F; and
n = 0 or 2.

38. The composition of claim 29 where the compound is 4(or 5)-(3,4-dichlorophenyl)-5(or 4)-phenyl-2-(1,1,2,2-tetrafluoroethylsulfonyl)imidazole.

39. The composition of claim 30 where the compound is 4,5-bis(4-fluorophenyl)-2-(1,1,2,2-tetrafluoroethylsulfonyl)imidazole.

40. The composition of claim 30 where the compound is 4(or 5)-4-fluorophenyl)-5(or 4)-phenyl-2-(1,1,2,2-tetrafluoroethylsulfonyl)imidazole.

41. The composition of claim 30 where the compound is 4,5-bis(4-chlorophenyl)-2-(1,1,2,2-tetrafluoroethylsulfonyl)imidazole.

42. The composition of claim 30 where the compound is 4(or 5)-(4-chlorophenyl)-5(or 4)-phenyl-2-(1,1,2,2-tetrafluoroethylsulfonyl)imidazole.

43. The composition of claim 30 where the compound is 4,5-diphenyl-2-(1,1,2,2-tetrafluoroethylsulfonyl)imidazole.

44. The composition of claim 30 where the compound is 4,5-diphenyl-2-(1,1,2,2-tetrafluoroethylthio)imidazole.

45. The composition of claim 30 where the compound is 4,5-diphenyl-2-trifluoromethylsulfonylimidazole.

46. The composition of claim 30 where the compound is 4,5-bis(p-fluorophenyl)-2-trifluoromethylthioimidazole.

47. The composition of claim 30 where the compound is 4,5-bis(p-fluorophenyl)-2-trifluoromethylsulfonylimidazole.

48. A pharmaceutical composition comprising a suitable pharmaceutical carrier and an effective analgesic amount of the compound of claim 21.

49. A pharmaceutical composition comprising a suitable pharmaceutical carrier and an effective analgesic amount of the compound of claim 22.

50. A pharmaceutical composition comprising a suitable pharmaceutical carrier and an effective analgesic amount of the compound of claim 23.

51. A phamaceutical composition comprising a suitable pharmaceutical carrier and an effective analgesic amount of the compound of claim 24.

52. A pharmaceutical composition comprising a suitable pharmaceutical carrier and an effective analgesic amount of the compound of claim 25.

53. A pharmaceutical composition comprising a suitable pharmaceutical carrier and an effective analgesic amount of the compound of claim 26.

54. A pharmaceutical composition comprising a suitable pharamceutical carrier and an effective analgesic amount of the compound of claim 27.

55. A pharmaceutical composition comprising a suitable pharmaceutical carrier and an effective analgesic amount of the compound of claim 28.

56. A method of treating arthritis in a mammal which comprises administering to the mammal an effective anti-arthritic amount of a compound of the formula

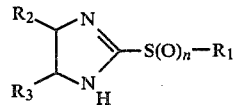

where
n = 0, 1, or 2;
$R_1 = C_1-C_8$ alkyl; allyl; vinyl; $-CH_2COCH_3$; $-CH_2S(O)_m CH_3$, where m = 0, 1, or 2; mono- or polyhalo- $C_1-C_8$ alkyl;
$R_2$ and $R_3$, the same or different =

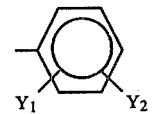

$Y_1$ and $Y_2$, the same or different = hydrogen, $C_1-C_4$ alkoxy, acetoxy, $C_1-C_4$ alkyl, Cl, F, $CF_3$, $-N(CH_3)_2$, $NO_2$, $CH_3S-$, $CH_3SO_2-$, or $Y_1$ and $Y_2$ taken together forming a dioxymethylene bridge;
provided, when $R_1 = C_1-C_8$ alkyl, $C_3-C_4$ haloalkyl with the halogen substituted at the 3 through 8 position, allyl, or $-CH_2COCH_3$ both $Y_1$ and $Y_2$ cannot be H;
its pharmaceutically suitable acid addition salt where n = 0 or its pharmaceutically suitable metal salt where n = 1 or 2.

57. The method of claim 56 where
n = 0, 1, or 2;
$R_1 = C_1-C_4$ alkyl; allyl; $-CH_2COCH_3$; $-CH_2S(O)_m CH_3$, where m = 0, 1, or 2; mono- or polyfluoro- $C_1-C_4$ alkyl;
$R_2$ and $R_3$, the same or different =

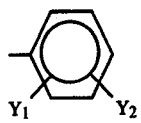

$Y_1$ and $Y_2$, the same or different = hydrogen, methoxy, ethoxy, acetoxy, $C_1$-$C_4$ alkyl, Cl, F, $CF_3$, —$N(CH_3)_2$, or $Y_1$ and $Y_2$ taken together forming a dioxymethylene bridge;

provided, when $R_1 = C_1$-$C_4$ alkyl, $C_3$-$C_4$ fluoroalkyl with the fluorine substituted at the 3 or 4 position, allyl, or —$CH_2COCH_3$, both $Y_1$ and $Y_2$ cannot be H.

58. The method of claim 56 where $R_1 = $ —$CF_2CF_2H$.
59. The method of claim 56 where $R_1 = $ —$CF_3$.
60. The method of claim 56 where $R_2$ and $R_3$ independently =

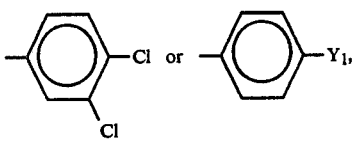

where $Y_1 = $ H, Cl, or F.

61. The method of claim 56 where n=1 or 2.
62. The method of claim 57 where
$R_1 = $ —$CF_2CF_2H$;
$R_2$ and $R_3$, independently, =

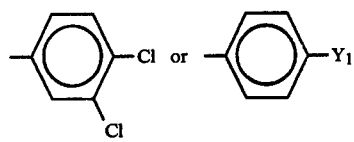

where
$Y_1 = $ H, Cl, or F.; and
n=0, 1 or 2.

63. The method of claim 57 where
$R_1 = $ —$CF_2CF_2H$;
$R_2$ and $R_3$, independently, =

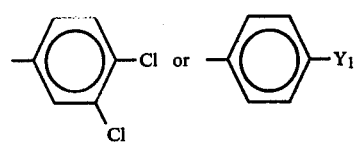

where
$Y_1 = $ H, Cl, or F.; and
n=0 or 2.

64. The method of claim 57 where
$R_1 = $ —$CF_3$;
$R_2$ and $R_3$, independently, =

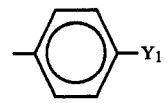

where $Y_1 = $ H, Cl, or F.; and
n=0, 1 or 2.

65. Th method of claim 56 where the compound is 4(or 5)-(3,4-dichlorophenyl)-5(or 4)-phenyl-2-(1,1,2,2-tetrafluoroethylsulfonyl)imidazole.

66. The method of claim 57 where the compound is 4,5-bis(4-fluorophenyl)-2-(1,1,2,2-tetrafluoroethylsulfonyl)imidazole.

67. The method of claim 57 where the compound is 4(or 5)-(4-fluorophenyl)-5(or 4)-phenyl-2-(1,1,2,2-tetrafluoroethylsulfonyl)imidazole.

68. The method of claim 57 where the compound is 4,5-bis(4-chlorophenyl)-2-(1,1,2,2-tetrafluoroethylsulfonyl)imidazole.

69. The method of claim 57 where the compound is 4(or 5)-(4-chlorophenyl)-5(or 4)-phenyl-2-(1,1,2,2-tetrafluoroethylsulfonyl)imidazole.

70. The method of claim 57 where the compound is 4,5-diphenyl-2-(1,1,2,2-tetrafluoroethylsulfonyl)imidazole.

71. The method of claim 57 where the compound is 4,5-diphenyl-2-(1,1,2,2-tetrafluoroethylthio)imidazole.

72. The compound of claim 57 where the compound is 4,5-diphenyl-2-trifluoromethylsulfonylimidazole.

73. The method of claim 57 where the compound is 4,5-bis(p-fluorophenyl)-2-trifluoromethylthioimidazole.

74. The method of claim 57 where the compound is 4,5-bis(p-fluorophenyl)-2-trifluoromethylsulfonylimidazole.

75. A method of alleviating pain in a mammal which comprises administering to the mammal an effective analgesic amount of a compound of claim 21.

76. A method of alleviating pain in a mammal which comprises administering to the mammal an effective analgesic amount of a compound of claim 22.

77. A method of alleviating pain in a mammal which comprises administering to the mammal an effective analgesic amount of the compound of claim 23.

78. A method of alleviating pain in a mammal which comprises administering to the mammal an effective analgesic amount of the compound of claim 24.

79. A method of alleviating pain in a mammal which comprises administering to the mammal and ffective analgesic amount of the compound of claim 25.

80. A method of alleviating pain in a mammal which comprises administering to the mammal an effective analgesic amount of the compound of claim 26.

81. A method of alleviating pain in a mammal which comprises administering to the mammal an effective analgesic amount of the compound of claim 27.

82. A method of alleviating pain in a mammal which comprises administering to the mammal an effective analgesic amount of the compound of claim 28.

* * * * *